US00PP23814P2

(12) United States Plant Patent
Hartman

(10) Patent No.: US PP23,814 P2
(45) Date of Patent: Aug. 6, 2013

(54) ***CALADIUM* PLANT NAMED 'TENDERNESS'**

(50) Latin Name: *Caladium×hortulanum*
Varietal Denomination: Tenderness

(76) Inventor: Robert Dale Hartman, Lake Placid, FL (US)

( * ) Notice: Subject to any disclaimer, the term of this patent is extended or adjusted under 35 U.S.C. 154(b) by 4 days.

(21) Appl. No.: 13/374,452

(22) Filed: Dec. 29, 2011

(51) Int. Cl.
*A01H 5/00* (2006.01)

(52) U.S. Cl.
USPC ..... Plt./373

(58) Field of Classification Search
USPC ..... Plt./373
See application file for complete search history.

*Primary Examiner* — Kent L Bell
(74) *Attorney, Agent, or Firm* — C. A. Whealy

(57) ABSTRACT

A new and distinct cultivar of *Caladium* plant named 'Tenderness', characterized by its compact and mounding plant habit; short plant size; uniform plant habit; vigorous and dense growth habit; lance-type leaves with light to greyed green-colored venation, light red purple-colored interveinal areas and dark green-colored borders and margins; and good landscape performance.

4 Drawing Sheets

Botanical designation: *Caladium×hortulanum.*
Cultivar denomination: 'TENDERNESS'.

BACKGROUND OF THE INVENTION

The present invention relates to a new and distinct cultivar of *Caladium* plant, botanically known as *Caladium×hortulanum*, commercially referred to as a lance leaf-type *Caladium* and hereinafter referred to by the name 'Tenderness'.

The objective of the Inventor's breeding program is to create new *Caladium* plants that have uniform plant habit, exceptional container and garden performance and attractive foliage coloration.

The new *Caladium* plant originated from a cross-pollination made by the Inventor in April, 2002 in Lake Placid, Fla. of *Caladium×hortulanum* 'Pink Symphony', not patented, as the female, or seed, parent with *Caladium×hortulanum* 'White Wing', not patented, as the male, or pollen, parent. The new *Caladium* plant was discovered and selected by the Inventor as a single plant within the progeny of the stated cross-pollination in a controlled outdoor nursery environment in Lake Placid, Fla. on Jun. 15, 2003.

Asexual reproduction of the new *Caladium* plant by 'chipping' the tubers (cutting the tuber into segments each segment containing an axillary bud and tuber cortical tissue) in a controlled outdoor nursery environment in Lake Placid, Fla. since Apr. 15, 2004 has shown that the unique features of this new *Caladium* plant are stable and reproduced true to type in successive generations of asexual reproduction.

SUMMARY OF THE INVENTION

Plants of the new *Caladium* have not been observed under all possible environmental conditions and cultural practices. The phenotype may vary somewhat with variations in environmental conditions such as temperature and light intensity, without, however, any variance in genotype.

The following traits have been repeatedly observed and are determined to be the unique characteristics of 'Tenderness'. These characteristics in combination distinguish 'Tenderness' as a new and distinct *Caladium* plant:

1. Compact and mounding plant habit; short plant size.
2. Uniform plant habit.
3. Vigorous and dense growth habit.
4. Lance-type leaves with light to greyed green-colored venation, light red purple-colored interveinal areas and dark green-colored borders and margins.
5. Good landscape performance.

Plants of the new *Caladium* differ primarily from plants of the female parent, 'Pink Symphony', in the following characteristics:

1. Plants of the new *Caladium* are more compact than plants of 'Pink Symphony'.
2. Plants of the new *Caladium* grow faster than plants of 'Pink Symphony'.
3. Leaves of plants of the new *Caladium* are more oval than and not as elongate as leaves of plants of 'Pink Symphony'.
4. Plants of the new *Caladium* and 'Pink Symphony' differ in leaf coloration as leaves of plants of 'Pink Symphony' have green-colored venation, deep pink-colored interveinal areas and green-colored borders.

Plants of the new *Caladium* differ primarily from plants of the male parent, 'White Wing', in the following characteristics:

1. Plants of the new *Caladium* are more compact than and not as upright as plants of 'White Wing'.
2. Leaves of plants of the new *Caladium* are broader than leaves of plants of 'White Wing'.
3. Plants of the new *Caladium* and 'White Wing' differ in leaf coloration as leaves of plants of 'White Wing' have white-colored venation and interveinal areas with mottled light and dark green-colored borders.

Plants of the new *Caladium* can be compared to plants of *Caladium* 'Thai Beauty', not patented. In side-by-side comparisons conducted in Avon Park, Fla., plants of the new *Caladium* differed primarily from plants of 'Thai Beauty' in the following characteristics:

1. Plants of the new *Caladium* were compact and denser than plants of 'Thai Beauty'.
2. Plants of the new *Caladium* grew faster than plants of 'Thai Beauty'.

3. Leaves of plants of the new *Caladium* were more rounded and broader than leaves of plants of 'Thai Beauty'.
4. Plants of the new *Caladium* and 'Thai Beauty' differed in leaf coloration as leaves of plants of 'Thai Beauty' had white and green-colored venation, deep pink-colored interveinal areas and green-colored margins.

Plants of the new *Caladium* can also be compared to plants of *Caladium* 'Florida Sweetheart', disclosed in U.S. Plant Pat. No. 8,526. In side-by-side comparisons conducted in Avon Park, Fla., plants of the new *Caladium* differed primarily from plants of 'Florida Sweetheart' in the following characteristics:

1. Plants of the new *Caladium* were more compact than plants of 'Florida Sweetheart'.
2. Plants of the new *Caladium* grew slower than plants of 'Florida Sweetheart'.
3. Leaves of plants of the new *Caladium* were more round and smoother than leaves of plants of 'Florida Sweetheart'.
4. Plants of the new *Caladium* and 'Florida Sweetheart' differed in leaf coloration as leaves of plants of 'Florida Sweetheart' had dark pink-colored venation, rose pink-colored interveinal areas surrounded by thin green-colored borders.

BRIEF DESCRIPTION OF THE PHOTOGRAPHS

The accompanying photographs illustrate the overall appearance of the new *Caladium* plant showing the colors as true as it is reasonably possible to obtain in colored reproductions of this type. Colors in the photographs may differ slightly from the color values cited in the detailed botanical description which accurately describe the colors of the new *Caladium* plant.

The photograph at the top of the first sheet is a side perspective view of a typical plant of 'Tenderness' grown in a 15-cm container in a shadehouse.

The photograph at the bottom of the first sheet is a comparison view of potted plants of 'Tenderness' grown in 15-cm containers, the plant on the left has had its tuber de-eyed and the plant on the right has not had its tuber de-eyed prior to planting.

The photograph at the top of the second sheet is a top perspective view of typical plants of 'Tenderness' grown in an outdoor nursery.

The photograph at the bottom of the second sheet is a close-up view of typical freshly-harvested tubers and roots of 'Tenderness'.

The photograph on the third sheet is a close-up view of typical inflorescences of 'Tenderness'.

The photograph at the top of the fourth sheet is a comparison view of typical potted plants of the male parent, 'White Wing' (left), 'Tenderness' (center) and the female parent, 'Pink Symphony' (right).

The photograph at the bottom of the fourth sheet is a comparison view of typical potted plants of 'Thai Beauty' (lower left), 'Tenderness' (center) and 'Florida Sweetheart' (lower right).

DETAILED BOTANICAL DESCRIPTION

The aforementioned photographs and following observations and measurements describe plants grown during the spring in 15-cm containers in Avon Park, Fla. in a polypropylene-covered shadehouse (30% shade) and plants grown during the autumn in ground beds in an outdoor nursery in Zolfo Springs, Fla. All plants were grown under environmental conditions and cultural practices which approximate those generally used in commercial shadehouse and outdoor nursery *Caladium* production. During the production of the plants, day temperatures ranged from about 28° C. to 33° C. (shadehouse) or 29° C. to 35° C. (outdoor nursery), night temperatures ranged from about 22° C. to 25° C. (shadehouse) or 23° C. to 26° C. (outdoor nursery) and light levels were about 8,000 foot-candles (shadehouse) or 10,000 to 12,000 foot-candles (outdoor nursery). Plants grown in the shadehouse were eight weeks old when the photographs and the detailed description were taken. Plants grown in the outdoor nursery were six months old when the photographs and the detailed description were taken. In the following description, color references are made to The Royal Horticultural Society Colour Chart, 2001 Edition, except where general terms of ordinary dictionary significance are used.

Botanical classification: *Caladium×hortulanum* 'Tenderness'.

Parentage:

*Female, or seed, parent.*—*Caladium×hortulanum* 'Pink Symphony', not patented.

*Male, or pollen, parent.*—*Caladium×hortulanum* 'White Wing', not patented.

Propagation:

*Type.*—By "chipping" the tubers.

*Time to initiate roots, summer.*—About seven to ten days at 32° C.

*Time to initiate roots, winter.*—About two to three weeks at 24° C.

*Tuber description* (*outdoor nursery-grown plants*).—Appearance: Multi-segmented; individual segments ovate in shape. Height: About 3.3 cm. Diameter: About 5.3 cm. Texture: Thick and starchy; somewhat brittle. Color: Epidermis, freshly harvested, close to 199D and 159B to 159C tinged with close to 56D; epidermis, dried tuber, close to 200A to 200B; interior, close to 3D; axillary buds, close to 155C to 155D. Root description: Thick, fleshy contractile roots; color, close to 155C. Rooting habit: Few lateral branches; moderately dense.

Plant description:

*Plant type.*—Herbaceous perennial; suitable as a potted plant in containers 15-cm to 25-cm and suitable as a landscape plant in shaded areas.

*Plant and growth habit.*—Compact and mounding plant habit; short plant size; inverted triangle; vigorous and dense growth habit; rapid growth rate; petioles and leaves arise from one or more growing points on tubers; petioles mostly upright and slightly leaning outwardly with development.

*Plant height, from soil level to top of foliar plane, shadehouse-grown potted plants.*—About 18 cm to 21 cm.

*Plant height, from soil level to top of inflorescences, shadehouse-grown potted plants.*—About 27 cm.

*Plant diameter or spread, shadehouse-grown potted plants.*—About 40 cm to 46 cm.

*Number of clumps per plant, shadehouse-grown potted plants.*—About seven from de-eyed tubers.

*Cataphylls, shadehouse-grown potted plants.*—Length: About 4.5 cm to 8 cm. Width: About 1.5 cm to 1.9 cm. Shape: Deltoid. Apex: Cuspidate. Base: Sheathing the stem. Color, outer surface: Close to N170D tinged with close to 148B, streaked and speckled with close to 147A tinged with close to N199B; with development, color becoming closer to 200C. Color, inner surface: Close to N155C; colors and patterns visible from outer surface.

Foliage description:

*Length, shadehouse-grown potted plants*.—About 14 cm to 19 cm.

*Width, shadehouse-grown potted plants (flattened)*.—About 8.5 cm to 12.5 cm.

*Shape*.—Ovate.

*Apex*.—Acuminate.

*Base*.—Sagittate to cordate.

*Margin*.—Entire; broad undulations.

*Texture, upper surface*.—Smooth, glabrous.

*Texture, lower surface*.—Smooth, glabrous; glaucous.

*Venation pattern*.—Pinnate.

*Color, shadehouse-grown potted plants*.—Developing leaves, upper surface: Basal notch: Close to 60A. Midrib: Close to 195D; distally, close to 147C to 147D. Primary and secondary venation: Close to 147C to 147D. Interveinal areas: Random sectors, close to 155C variably tinged with close to 53D; and close to 147A, 146B and 194D. Borders and margins: Close to 147A. Developing leaves, lower surface: Basal notch: Close to 60A. Midrib: Close to 145C tinged with close to N170D; distally, close to 147C. Primary and secondary venation: Close to 147C. Interveinal areas: Random sectors, close to 155C variably tinged with close to 53D; and close to 147B and N155D. Borders and margins: Close to 147B. Fully expanded leaves, upper surface: Basal notch: Close to 60A. Midrib: Close to 195D. Primary and secondary venation: Close to 147D. Interveinal areas: Random sectors, close to 155C variably tinged with close to 53D; and close to 53D. Borders and margins: Close to 147A. Fully expanded leaves, lower surface: Midrib: Close to 145C tinged with close to N170D. Primary and secondary venation: Close to 146D. Interveinal areas: Random sectors, close to 155C variably tinged with close to 53D. Borders and margins: Close to 147B.

*Petiole*.—Aspect: Mostly erect, leaning and curving outwardly with development; flexible. Length, shadehouse-grown potted plants: About 14 cm to 16.5 cm. Diameter, distal, shadehouse-grown potted plants: About 3 mm to 3.8 mm. Diameter, proximal, shadehouse-grown potted plants: About 6 mm to 9.5 mm. Color, shadehouse-grown potted plants: Close to 199D and N170D tinged with close to 148B, densely streaked and speckled with close to N199B tinged with close to 147A; below the leaf/petiole junction, close to 147B. Wing length, shadehouse-grown potted plants: About 3 cm to 5 cm. Wing diameter, shadehouse-grown potted plants: About 7 mm to 9 mm. Wing color, shadehouse-grown potted plants, outer surface: Close to N170D tinged with close to 148B and streaked and speckled with close to 147A tinged with close to N199B. Wing color, shadehouse-grown potted plants, inner surface: Close to N155C; colors and patterns visible from outer surface.

Inflorescence description: Inflorescences observed on eight-week old shadehouse-grown potted plants.

*Inflorescence arrangement*.—Upright hooded spathes surrounding a columnar spadix borne on a tall upright scape; spadix with sessile, simple female and male flowers separated into two zones; female flowers arranged on the lower one-third of the spadix; male flowers arranged on the upper two-thirds of the spadix; sterile flowers develop at junction of female and male flower zones; near this junction, the spathe constricts and surrounds and encloses the female flowers; spathe open and cupped around male flowers.

*Fragrance*.—None detected.

*Natural flowering season/longevity*.—Plants of the new *Caladium* typically flower during the spring or early summer in central Florida; flowers develop about eight weeks after growth commences; inflorescences last about three days before fading; inflorescences persistent.

*Spathe*.—Length: About 10 cm; upper open length, about 7.5 cm and lower closed length, about 2.5 cm. Width, distal: About 2.8 cm. Width, proximal: About 2.4 cm. Width, at constriction: About 1.7 cm. Shape: Ovate to somewhat obovate. Apex: Acuminate. Base: Tapering to the peduncle. Margin: Entire; slightly reflexed. Texture, upper and lower surfaces: Smooth, glabrous. Color, front surface, fully opened: Upper two-thirds: Close to 155B faintly tinged with close to 56D; with development, color becoming closer to 199B and 200C. Lower one-third: Close to 148B to 148C with areas of close to 145C; lightly flushed with close to 187A towards the base; color does not change with development. Color, rear surface, fully opened: Upper two-thirds: Close to 155B tinged with close to 56D and variably marked with close to 144C and 147B. Lower one-third: Marbled with random areas close to 147A to 147B, 157A and 155A.

*Spadix*.—Length: About 6.9 cm. Length, male flower zone: About 4.6 cm. Length, sterile flower zone: About 9 mm. Length, female flower zone: About 1.4 cm. Diameter, male flower zone: About 1.1 cm. Diameter, sterile flower zone: About 7 mm. Diameter, female flower zone: About 8 mm. Shape: Columnar. Apex: Obtuse. Base: Obtuse. Aspect: Upright. Color, mature, male zone: Close to 11C tinged with close to 162D. Color, mature, sterile zone: Close to 11C tinged with close to 162D. Color, mature, female zone: Close to 155D. Male flowers: Quantity per spadix: About 169. Shape: Obovate. Height: About 3 mm. Diameter: About 3 mm. Pollen amount: None observed. Female flowers: Quantity per spadix: About 143. Shape: Obovate. Height: About 3 mm. Diameter: About 2 mm. Stigma color: Close to 155D. Ovary color: Close to 155C.

*Scape*.—Length: About 17 cm. Diameter: About 6.5 mm. Strength: Sturdy; flexible. Aspect: Erect or slightly curved. Texture: Smooth, glabrous; glaucous. Color: Close to 148A with longitudinal stripes (venation), close to 147A; just below the spathe, close to 147B.

*Seeds and fruits*.—Seed and fruit development have not been observed on plants of the new *Caladium*.

Disease & pest tolerance/resistance: Plants of the new *Caladium* have been observed to have above average tolerance to *Xanthomonas* Leaf Spot and average tolerance to *Pythium* Root Rot. Plants of the new *Caladium* have not been observed to have resistance to pests and other pathogens common to *Caladium* plants.

Temperature tolerance: Plants of the new *Caladium* have been observed to be tolerant to temperatures ranging from about 7° C. to about 40° C. and suitable for USDA Hardiness Zones 8A to 11.

It is claimed:

1. A new and distinct *Caladium* plant named 'Tenderness' as illustrated and described.

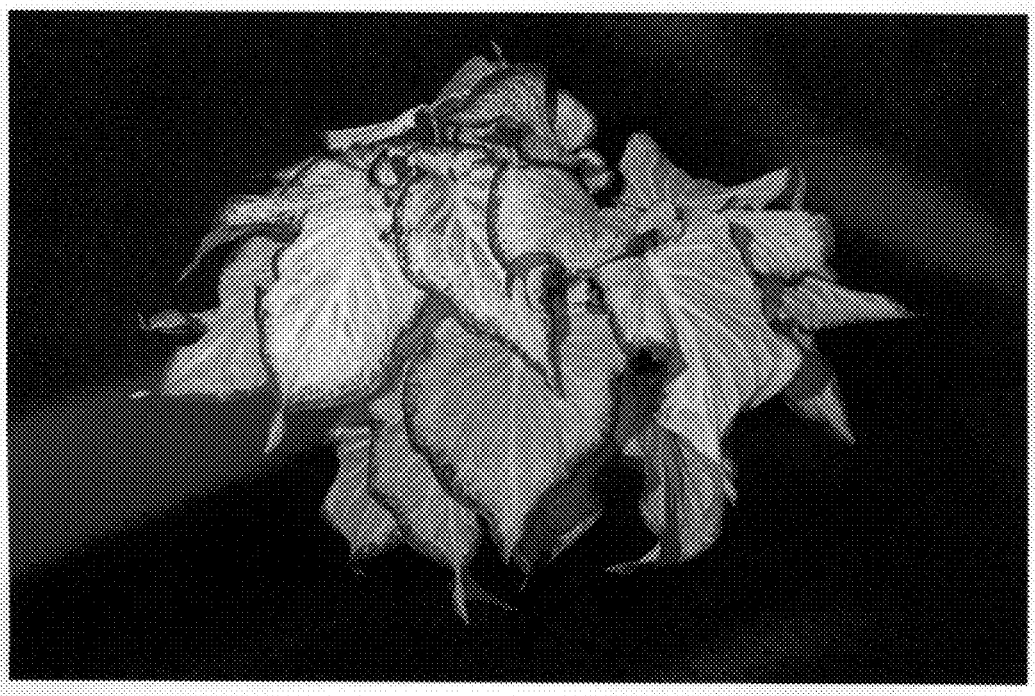
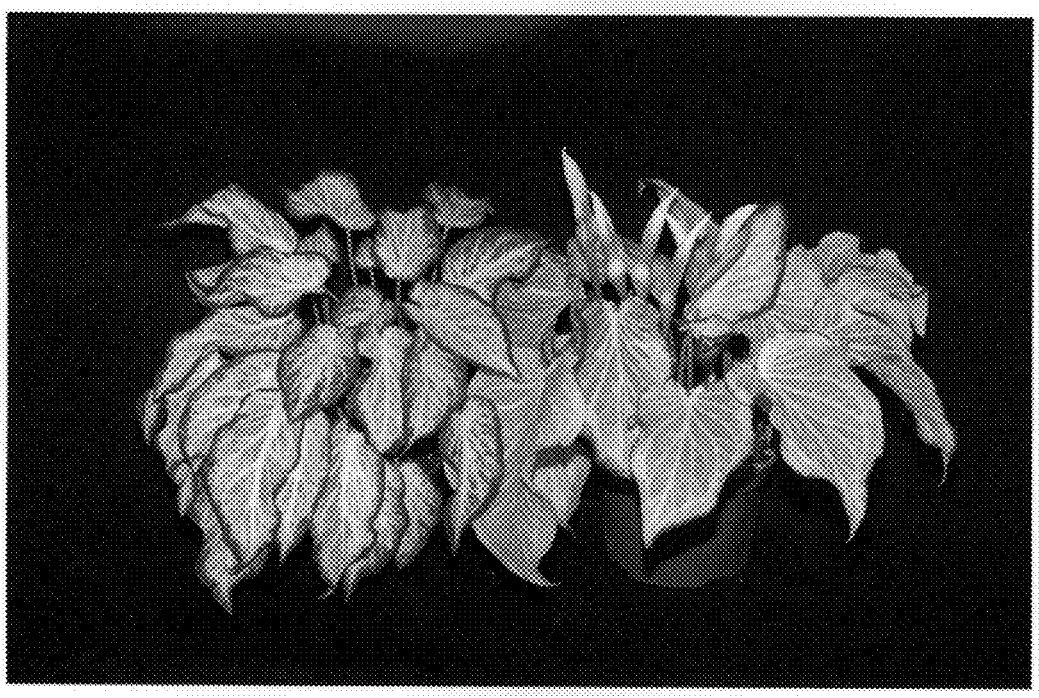

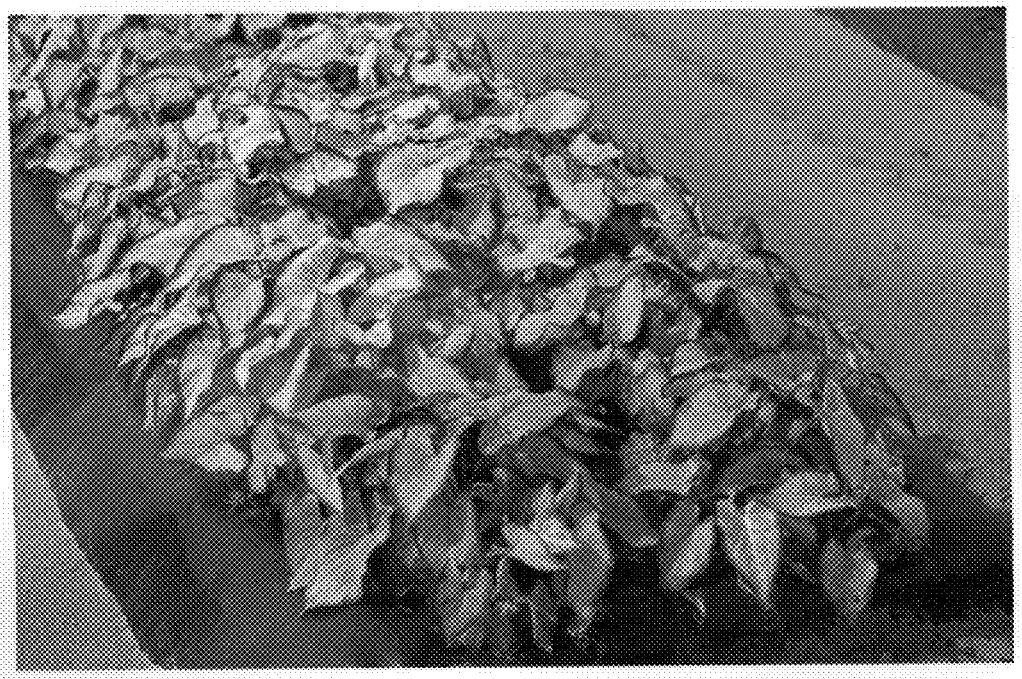
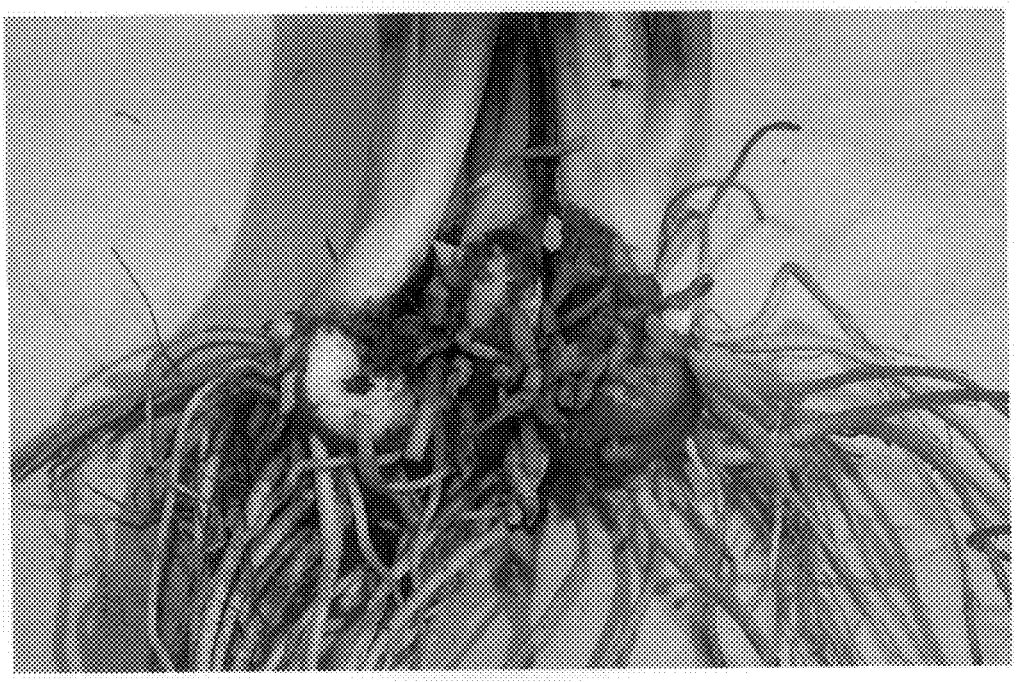

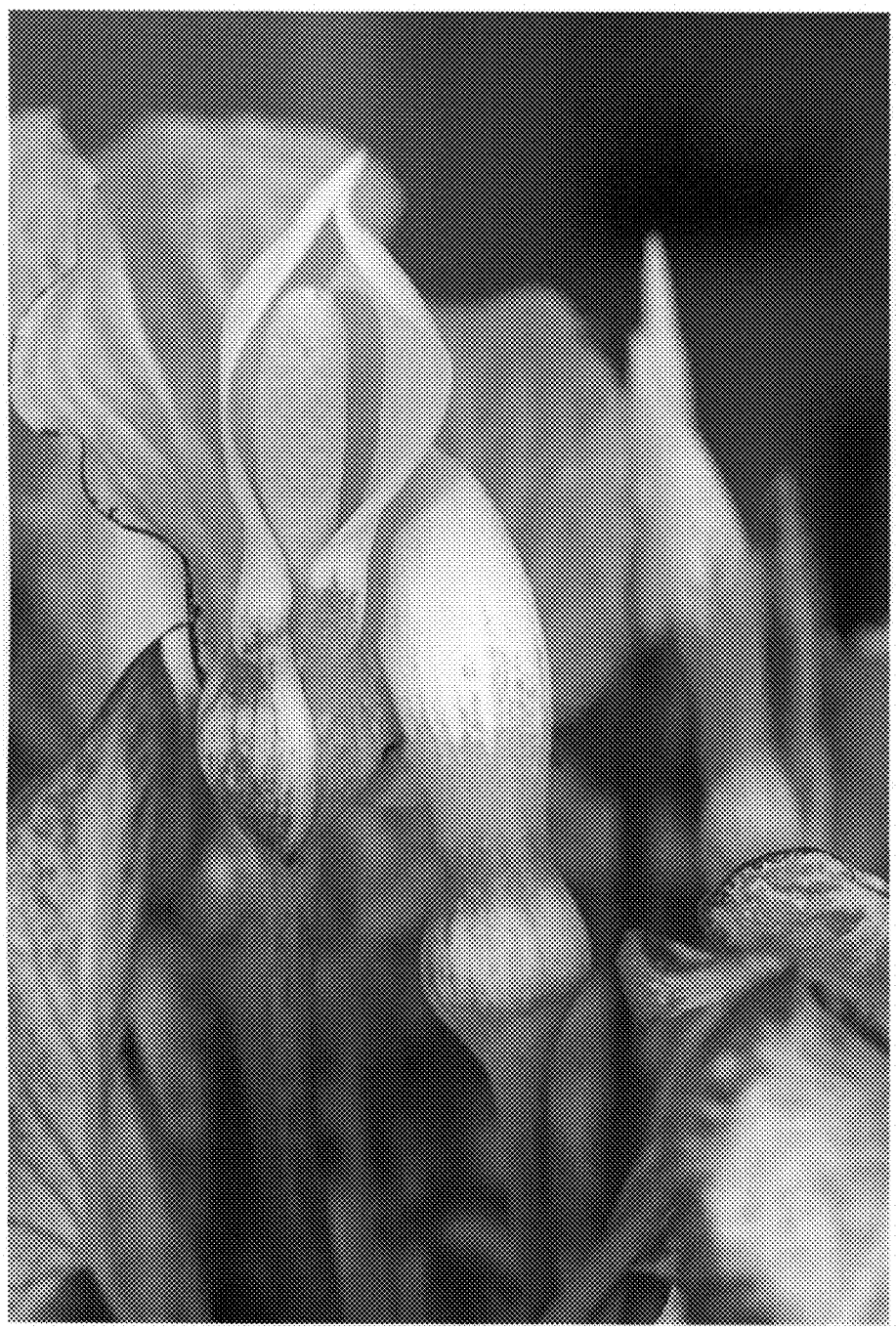

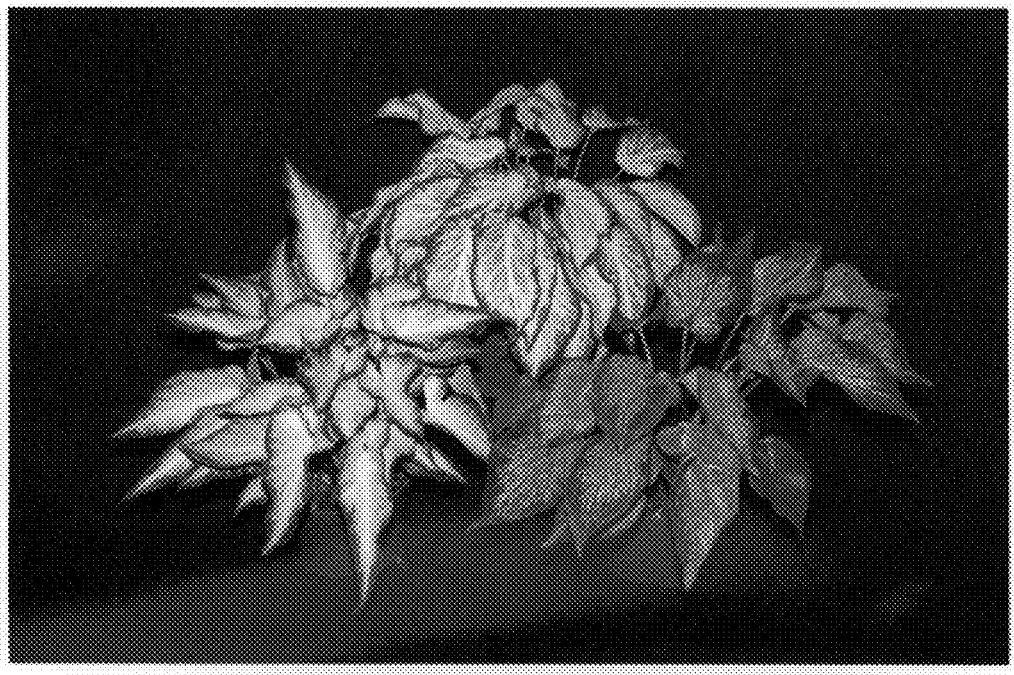
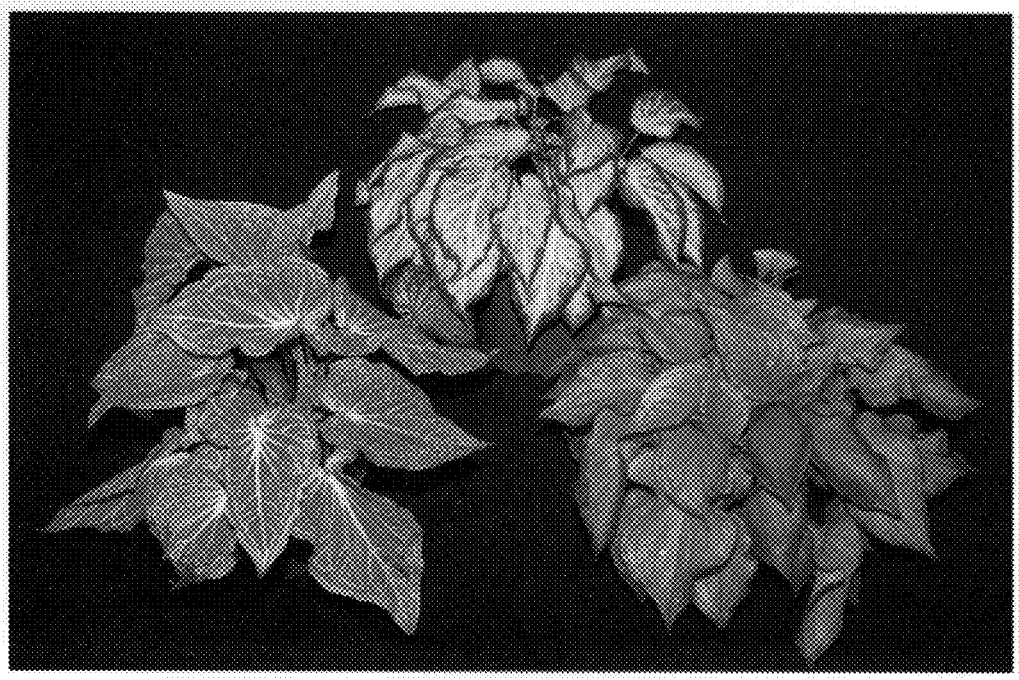

* * * * *